United States Patent [19]

Tanimoto et al.

[11] Patent Number: 4,610,541
[45] Date of Patent: * Sep. 9, 1986

[54] FOREIGN SUBSTANCE INSPECTING APPARATUS

[75] Inventors: Akikazu Tanimoto, Yokohama; Kazunori Imamura, Tokyo, both of Japan

[73] Assignee: Nippon Kogaku K. K., Tokyo, Japan

[*] Notice: The portion of the term of this patent subsequent to Aug. 28, 2001 has been disclaimed.

[21] Appl. No.: 596,440

[22] Filed: Apr. 3, 1984

[30] Foreign Application Priority Data

Apr. 7, 1983 [JP] Japan .................................. 58-61422

[51] Int. Cl.4 ........................................... G01N 21/88
[52] U.S. Cl. ................................... 356/237; 356/239; 250/563; 250/572
[58] Field of Search ................ 356/237, 239; 250/550, 250/562, 563, 572

[56] References Cited

U.S. PATENT DOCUMENTS 3,814,946 6/1974 Takahashi et al. .................. 250/572
3,984,189 10/1976 Seki et al. ......................... 356/237 X
4,173,441 11/1979 Wolf ................................. 250/563 X
4,342,515 8/1982 Akiba et al. ......................... 356/237
4,468,120 8/1984 Tanimoto et al. .................... 356/237

Primary Examiner—Vincent P. McGraw
Assistant Examiner—S. A. Turner
Attorney, Agent, or Firm—Shapiro and Shapiro

[57] ABSTRACT

An inspecting apparatus for precisely detecting foreign substances or scars present on a translucent planar article such as a photomask at a high speed with a laser beam entering from face of the article, comprises first photoelectric means for receiving the scattered light generated in a space on a face of the photomask, second photoelectric means for receiving the scattered light generated in a space on the other face of the photomask, comparator means for comparing the photoelectrically converted signals from the first and second photoelectric means to identify one of predetermined plural magnitude relationships to which the magnitudes of the signals belong, and inspecting means for generating, in response to the detection output signal of the comparator means, a detection signal allowing to identify the approximate difference in the shape of the foreign substance, for example either a tall foreign substance or a short one.

9 Claims, 22 Drawing Figures

FIG. 9
FIG. 10
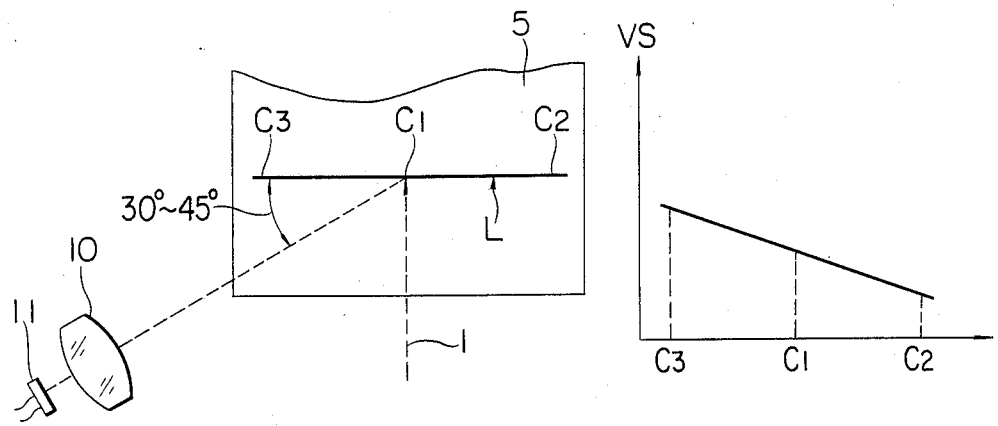
FIG. 11
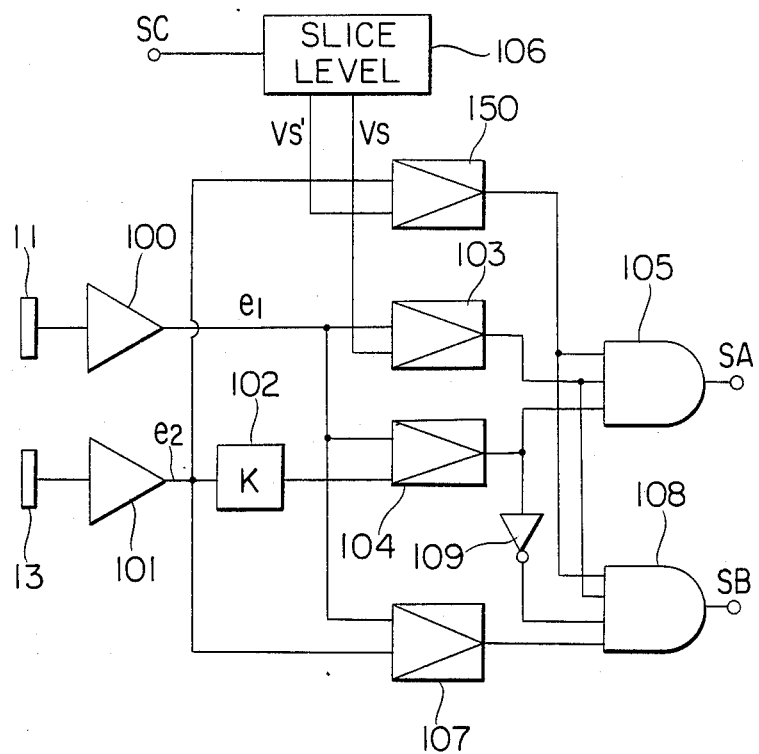

FOREIGN SUBSTANCE INSPECTING APPARATUS

BACKGROUND OF THE INVENTION

1. Field of the Invention

The present invention relates to an apparatus for detecting foreign substances such as minute dusts, and more particularly to such apparatus for detecting foreign substances attached on a planar substrate such as photomask or reticle for large-scale integrated circuit.

2. Description of the Prior Art

In the process of producing photomasks or wafers for large-scale integrated circuits, foreign substances may become attached to the reticle or masks and eventually cause defects in the produced masks or wafers. In a pattern exposure apparatus for reduction exposure of a reticle pattern onto a mask or of a mask pattern onto a wafer, there are produced plural chip patterns on a single mask or wafer, and strict inspection has to be carried out for such foreign substances in the production process since such defect appears commonly in all chip patterns of the mask or wafer. For this purpose there is usually considered visual inspection, but such inspecting operation requires many hours, thus leading to the fatigue of the inspecting personnel and to the loss of inspecting efficiency.

Recently there are therefore proposed various apparatus for automatically detecting such foreign substances attached to the mask or reticle for example by laser irradiation. The present inventors already proposed, in the U.S. patent application Ser. No. 343,552 filed Jan. 28, 1982, now Pat. No. 4,468,120, issued Aug. 28, 1984, an improvement on such apparatus to enable exact automatic detection of the foreign substance on the glass, thus allowing to identify whether the foreign substance is present on an opaque area such as chromium or on a translucent area of the glass, and, in the latter case, whether the foreign substance is present on a surface of the inspected article at the incident side of the laser beam or on the other surface. It is however not yet possible to identify the attaching state of the foreign substance, namely the shape thereof or the status thereof on the surface, nor to distinguish a scar on the glass surface from the foreign substance.

SUMMARY OF THE INVENTION

An object of the present invention is to provide an inspecting apparatus capable of precisely detecting foreign substances or scars present on a translucent article at a high speed, and another object of the present invention is to provide an inspecting apparatus capable of identifying the approximate shape of the foreign substances.

The foregoing objects can be achieved, according to the present invention, by an apparatus in which a translucent planar article such as a photomask is scanned for example with a laser beam entering from a face of said article, and which comprises first photoelectric means for receiving the scattered light generated in a space on a face of said photomask, second photoelectric means for receiving the scattered light generated in a space on the other face of said photomask, comparator means for comparing the photoelectrically converted signals from said first and second photoelectric means to identify one of predetermined plural magnitude relationships to which the magnitudes of said signals belong, and inspecting means for generating, in response to the detection output signal of said comparator means, a detection signal allowing to identify the approximate difference in the shape of the foreign substance, for example either a tall foreign substance or a short one.

In an embodiment of the present invention, there are provided a first comparator circuit for comparing a first photoelectric signal from the first photoelectric means and a second photoelectric signal from the second photoelectric means to identify that said first photoelectric signal is larger than said second photoelectric signal, and a second comparator circuit for detecting that said first photoelectric signal is larger than K times of said second photoelectric signal, thereby enabling inspection on the shape of the foreign substance from the detection output signals of said first and second comparator circuits.

In another embodiment of the present invention there is provided an inspecting apparatus capable of detecting the foreign substances present on both faces of a photomask by laser irradiation onto a face thereof and identifying whether the foreign substance is present on a pattern bearing face or the other face.

BRIEF DESCRIPTION OF THE DRAWINGS

FIG. 9 is a plan view showing a part of the apparatus shown in FIG. 6;

FIG. 10 is a chart showing the change of the slicing voltage;

FIG. 11 is a block diagram of a second embodiment of the detecting circuit;

DETAILED DESCRIPTION OF THE PREFERRED EMBODIMENTS

Prior to the description of the embodiments of the present invention, reference is at first made to FIGS. 1 to 5 showing the states of scattered light in response to the attaching states of foreign substances and the scars when an inspected article is irradiated with a light beam. It is assumed that the light beam diagonally enters the inspected article, in order to obtain a better separation between the scattered light from a foreign substance and that from an opaque area such as chromium than in the case of vertical entry of the light beam.

Figure 1:
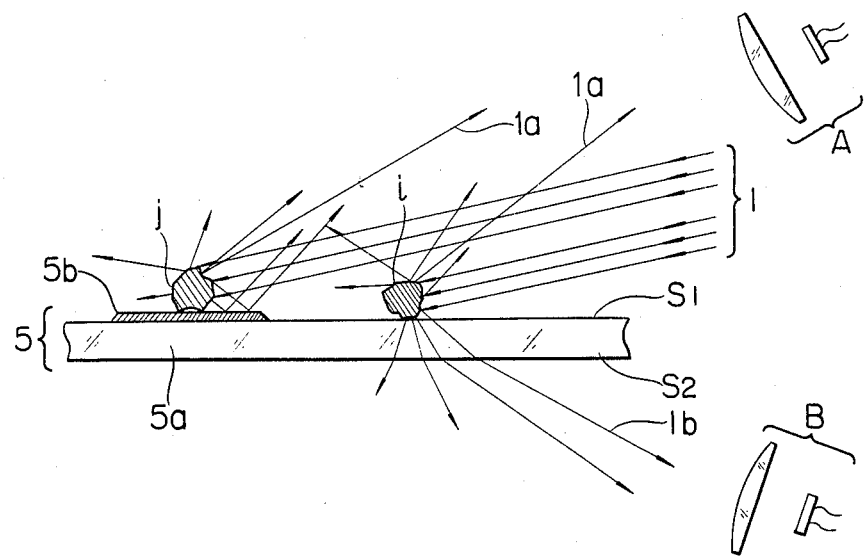
FIG. 1 is a view showing light scattering caused by a foreign substance present on a pattern bearing face.

FIG. 1 shows the light scattering by a foreign substance present on the glass substrate of a mask or a reticle (hereinafter collectively called photomask) and that by a foreign substance present on an opaque area of the photomask when a pattern bearing face thereof is irradiated with a laser light beam.

The laser beam 1 obliquely entering a face S1 of a glass plate 5a of a photomask 5 provided with an intimately attached opaque area 5b (said S1 being hereinafter called pattern bearing face) is normally reflected by the glass plate 5a or by the opaque area 5b. In the illustration there are only shown scattered lights except the laser beam 1. A photoreceptor A, composed of a condenser lens and a photoelectric element, is so positioned as not to receive the normally reflected laser beam, and as to obliquely look at an area irradiated by the laser beam 1 in order to minimize the reception of scattered light generated by minute surface irregularities of the pattern bearing face S1 of the glass plate 5a or the opaque area 5b. Also at a side of a rear face S2 opposite to the pattern bearing face S1 of the glass plate 5a, a photoreceptor B composed of a condenser lens and a photoelectric element is positioned symmetrically with respect to the glass plate 5a, particularly to the pattern bearing face S1 thereof, obliquely looking at the area irradiated by the laser beam 1 from the rear face side. Thus the photoreceptors A, B are so positioned as to receive the scattered light omnidirectionally generated from the foreign substance.

A foreign substance i attached on a translucent area of the glass plate 5a and a foreign substance j attached on the opaque area 5b generate photoelectric signals of substantially same magnitude from the photoreceptor A, since the foreign substances i, j, if of same dimension, generate omnidirectional scattered lights 1a of a same intensity. A part 1b of the scattered light from the foreign substance i reaches the photoreceptor B through the glass plate 5a. Though the scattered light 1b is generally weaker than the scattered light 1a, the photoreceptors A, B both generate certain photoelectric signals by the presence of the foreign substance i. On the other hand, the scattered light from the foreign substance j present on the opaque area 5b does not reach the photoreceptor B.

Thus the comparison of the photoelectric signals from the photoreceptors A, B allows to identify whether the foreign substance is present on the translucent area of the glass plate 5a or on the opaque area 5b thereof.

However, an edge of the opaque area 5b generate considerably strongly directional reflected light and omnidirectional scattered light. It is therefore necessary to position said photoreceptors A, B so as to only receive the scattered light, avoiding the directional reflected light from the edge, and to identify whether the received scattered light is from a foreign substance or from an edge. In this relation reference is made to FIG. 2, in which it is assumed that the photoreceptors A, B are positioned in the same manner as shown in FIG. 1.

The obliquely entering laser beam 1 is normally reflected on the pattern bearing face S1 of the photomask 5, but is scattered either by the foreign substance i or by an edge of the opaque area 5b constituting a circuit pattern. Since the opaque area 5b has a thickness of about 0.1 $\mu$m and is closely adhered to the pattern bearing face S1, scattered light 1c proceeding toward a space at the incident side of the laser beam 1 with respect to the glass plate 5a and scattered light 1d proceeding toward said glass plate 5a have a substantially same intensity. The scattered light 1d emerges from the rear face S2 of the glass plate 5a. On the other hand, since the foreign substance i generally has a dimension of several microns and is positioned higher from the surface S1, scattered light 1e proceeding from said surface S1 toward the interior of the glass plate 5a is weaker than scattered light 1f proceeding toward a space at the side of said face S1. This difference becomes more evident if the angle of the photoreceptors A, B to the pattern bearing face S1 becomes smaller. This phenomenon is also explicable from a fact that the scattered light behaves as a surfacial wave to the opaque area 5b closed adhered to the face S1 while the foreign substance i, only partially contacting the pattern bearing face S1 and mainly protruding into the surrounding space, causes light scattering in a free space, whereby the scattered light entering the pattern bearing face S1 with a small angle is mostly reflected at the pattern bearing face S1 and is little admitted into said face S1. Consequently it is possible to identify whether the scattered light is from a foreign substance or from an edge, by detecting the scattered light at the side of the pattern bearing face S1 with the photoreceptor A and the scattered light emerging from the rear face S2 with the photoreceptor B and by identifying whether the ratio of the intensities of the scattered lights exceeds for example 2.

Figure 3:
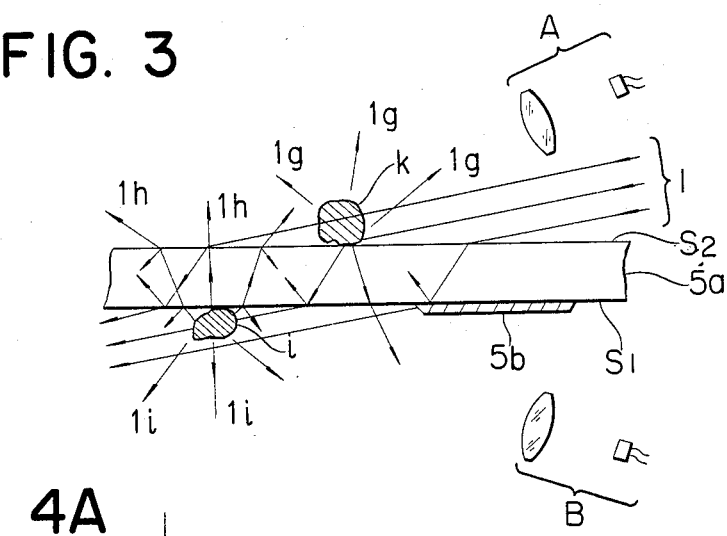
FIG. 3 is a view showing light scatterings caused by foreign substances present on a top face and a bottom face of the glass substrate.

Now reference is made to FIG. 3 showing the principle of identifying a foreign substance on the front face of the glass plate 5a from that on the rear face thereof. Also in FIG. 3 it is assumed that the photoreceptors A, B are positioned, as shown in FIG. 1, obliquely behind the photomask area irradiated by the laser beam 1, namely obliquely at the entering side of the laser beam 1, thus receiving so-called back scattering from the foreign substance.

Figure 4A:
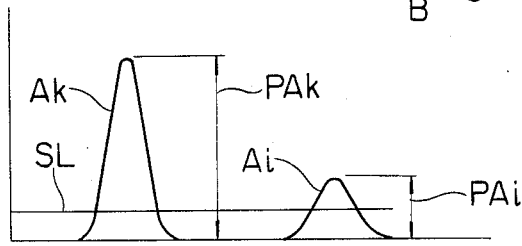
FIGS. 4A and 4B are views respectively showing signal wave forms in the photoreceptors A and B shown in FIG. 3.
Figure 4B:
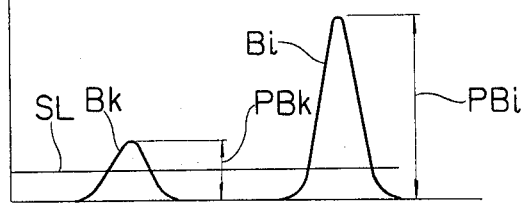

FIG. 3 shows, in case the laser beam 1 enters the rear face S2 of the photomask 5 not bearing the pattern, the difference between the scattering caused by a foreign substance k present on said rear face S2 and that caused by a foreign substance i present on the pattern bearing face S1. The laser beam 1 obliquely enters the rear face S2, and is partially reflected and partially transmitted to the pattern bearing face S1. Scattered light 1g generated by the foreign substance k is received by the photoreceptor A. Also among the scattered light generated by the foreign substance i present on the translucent area of the pattern bearing face S1, a part 1h emerges from the rear face S2 through the glass plate 5a and is received by said photoreceptor A. Among the scattered lights from the foreign substance i, the scattered light 1h, being subjected to losses by the reflection at the pattern bearing face S1 and the rear face S2, is weaker than the scattered light 1i not entering the interior of the glass plate 5a from the pattern bearing face S1. FIGS. 4A and 4B respectively show the output signals from the photoreceptors A, B when the entering position of the laser beam 1 on the photomask 5 is changed. In FIGS. 4A and 4B, the ordinate represents the level of the photoelectric signal proportional to the intensity of the scattered light received by the photoreceptors A, B, while the abscissa indicates time, of position of the laser spot on the photomask 5. In response to the scattering by the foreign substance k, the photoreceptors A, B respectively generate signals Ak, Bk with respective magnitudes PAk, PBk of which the former is 2 to 8 times larger than the latter. On the other hand, in response to the scattering by the foreign substance i, the photoreceptors A, B respectively generate signals Ai, Bi with respective magnitudes PAi, PBi, of which the latter is 2 to 8 times larger than the former. Thus the foreign substance is identified as present on the incident side of the laser beam 1, namely on the rear face S2 if the ratio of the output of the photoreceptor A to that of the photoreceptor B exceeds a constant K, for example 2, when the scattered light exceeds a certain level, for example a threshold level SL.

Figure 2:
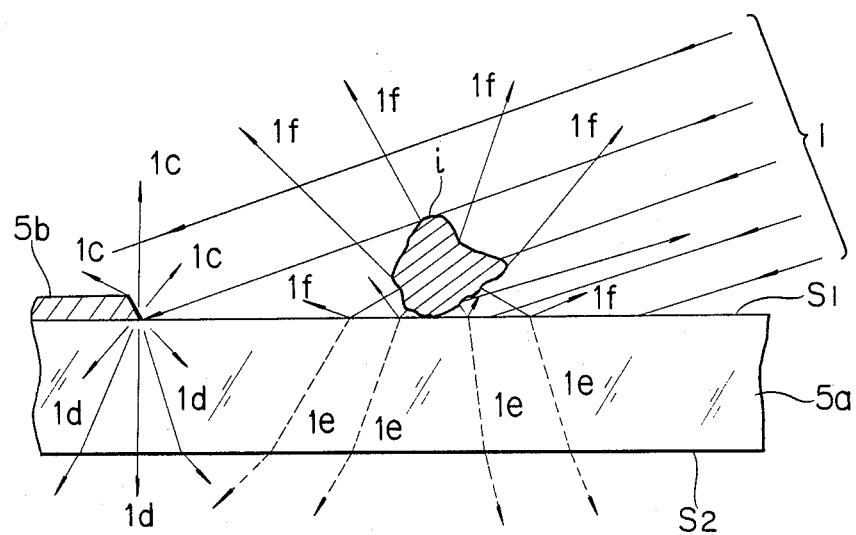
FIG. 2 is a view showing light scattering caused by a foreign substance present on a glass substrate and light scattering caused by a pattern edge.
Figure 5:
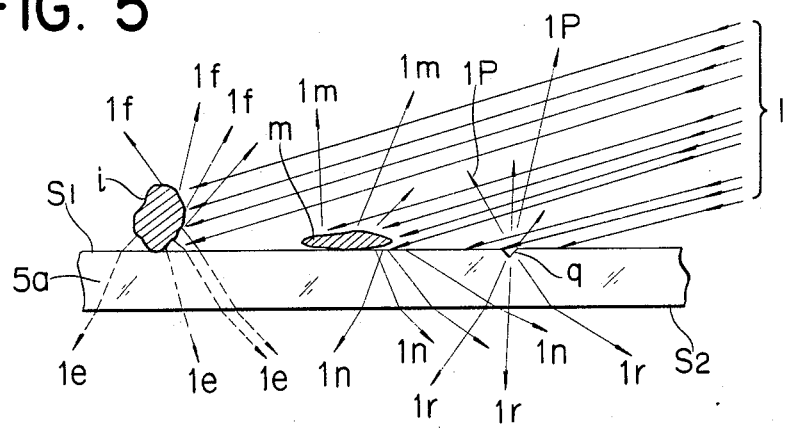
FIG. 5 is a view showing light scatterings caused by foreign substances of different shapes present on a glass substrate.

Now reference is made to FIG. 5 showing the difference in the scattering by foreign substances of difference shapes and by a scar. Photoreceptors A, B are positioned in the same manner as shown in FIGS. 1 to 3. In the foregoing explanation the foreign substance is assumed, as a foreign substance i shown in FIG. 3, to be partly contacting the glass plate 5a but mainly protruding therefrom. For this reason there is observed, as explained before, a large difference between scattered light 1f present in the space at the pattern bearing face S1 and scattered light 1e passing through the glass plate 5a and emerging in a space at the rear face S2. Such foreign substance i is generally dust or the like floating in the air and weakly adhered onto the photomask 5 and is generally dry, free from moisture or oil.

However, if the dust deposition takes place before the glass plate 5a becomes dry after washing thereof or if the washing water contains impurity, such dust or impurity forms a foreign substance m closely adhered to the glass plate 5a. Such lower foreign substance m with a larger contact area with the glass plate 5a, when irradiated with the laser beam 1, generates scattered light 1m, in the space at the pattern bearing face S1, of an intensity similar to that from the foreign substance i, and also scattered light 1n, in the space at the rear face S2, of a higher intensity than that of the scattered light 1e from said foreign substance i. It is therefore possible to distinguish the foreign substance m from the foreign substance i by determining the ratio of the photoelectric signal from the photoreceptor A receiving the scattered lights 1f, 1m to the photoelectric signal from the photoreceptor B receiving the scattered lights 1e, 1n.

A scar q present on the glass plate 5a of the photomask 5 as shown in FIG. 5 can be considered in a similar manner as an edge of the opaque area 5b of the pattern. The scar q generates, in response to the laser beam 1, scattered light 1P in the space at the pattern beam face S1 and scatter light 1r in the space at the rear face S2, both of high intensities, in a manner similar to the scattering by the aforementioned foreign substance m. This fact indicates a possibility of distinguishing the scattered light of a scar from that of a tall foreign substance, as in the separation of the scattered light of an edge of the opaque area 5b from that of the tall foreign substance i, thus avoiding erroneous detection of a scar as a tall foreign substance and enabling exact detection of the foreign substances alone.

Now there will be given an explanation on the inspecting apparatus of the present invention employing the principles explained in the foregoing.

Figure 6:
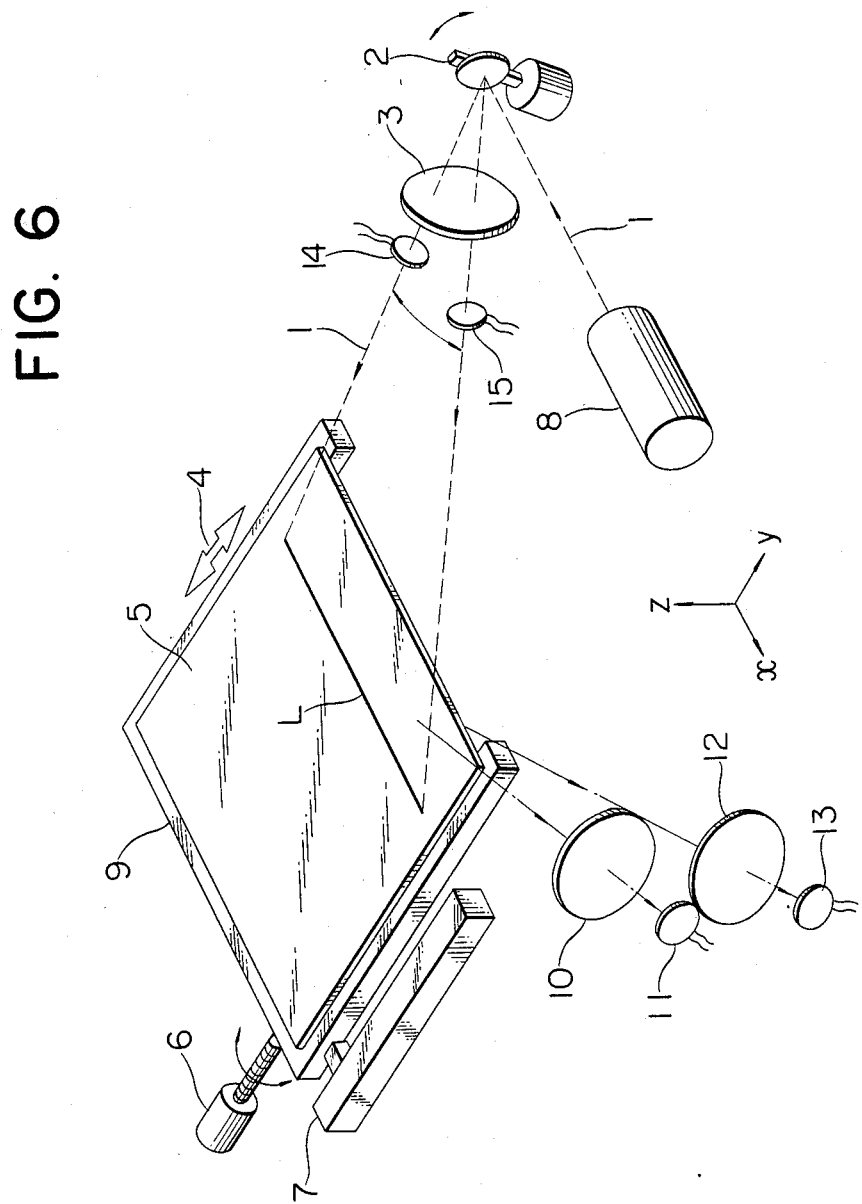
FIG. 6 is a perspective view of a first embodiment of the apparatus of the present invention.

FIG. 6 shows an embodiment suitable for inspecting a glass plate with patterns or a mask with relatively simple patterns, rather than photomasks with complicated patterns.

In FIG. 6, a photomask 5, constituting the article to be inspected, is supported by the peripheral areas on a support member 9, which is one-dimensionally movable, as indicated by an arrow 4, by means for example of a motor 6 and a driving screw. The pattern bearing face of said photomask 5 is defined as x-y plane of an x-y-z coordinate system. The amount of movement of the support member 9 is measured by a position detector 7 such as a linear encoder. A laser beam 1 from a laser unit 8 is converted into a desired diameter for example by an unrepresented expander and a condenser lens 3, thus increasing the light intensity per unit area. Said laser beam 1 scans a range L in the x-direction on the photomask 5 by means of a scanner 2 composed for example of a vibrator, a galvanomirror or a polygonal mirror. The scanning laser beam 1 enters the surface (x-y plane) of the photomask 5 with an incident angle of 70°-80°. Consequently the irradiated area on the photomask 5 is an oval spot extending approximately in the y-direction. Thus the laser beam 1 scans, by the scanner 2, a strip-shaped area of a length L in the x-direction and a determined width in the y-direction on the photomask 5. The laser beam 1 is focused on the face at the beam incident side of the photomask 5. In order to scan the entire surface of the photomask 5, the aforementioned motor 6 is simultaneously activated thus moving the photomask 5 in the y-direction at a speed smaller than the scanning speed of the laser beam 1. The position sensor 7 releases a signal indicating the irradiating position of the laser beam in the y-direction on the photomask 5.

In order to receive information from the foreign substances on the photomask 5, namely omnidirectionally scattered light, there are provided photoreceptor elements 11, 13. The element 11, corresponding to the aforementioned photoreceptor A, is so positioned as to receive the scattered light generated in a space at the front side of the photomask 5 receiving the laser beam 1, while the element 13, corresponding to the aforementioned photoreceptor B, is so positioned as to receive the scattered light generated in a space at the rear face. Lenses 10, 12 respectively direct the scattered light from the scanning range L toward the photoreceptor elements 11, 13. The optical axis of the lens 10 is so positioned as to be slanted at an angle of 10°-30° to the x-y plane and to look at the approximate center of the scanning range L of the laser beam 1 from the front side of the photomask 5, while that of the lens 12 is so positioned as to be symmetrical to that of the lens 10 with respect to the x-y plane. Also the optical axes of said lenses 10, 12 are positioned oblique to the longitudinal direction of the scanning area L, with an angle of 30° to 45° to the x-z plane. Furthermore, in order to detect the start and the end of each scanning by the laser beam 1, there are provided photoelectric elements 14, 15 at the lateral ends of the scanning optical path of the laser beam 1.

Figure 7:
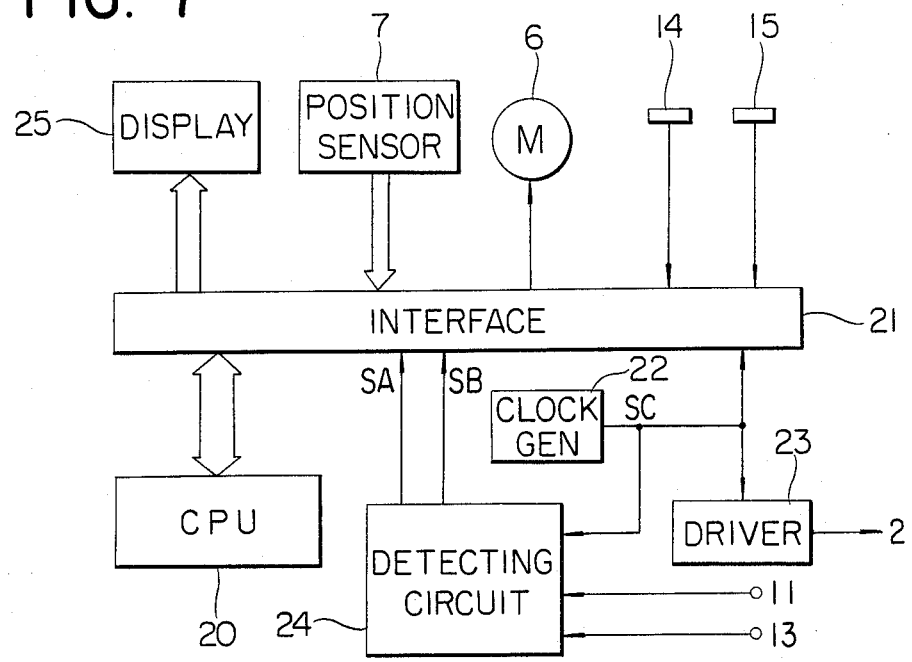
FIG. 7 is a block diagram of a device for controlling the apparatus shown in FIG. 6.

The apparatus shown in FIG. 6 is controlled by a central processing unit (CPU) 20 shown in FIG. 7. The CPU 20, equipped with a processing unit and memories as in the known microcomputers, releases instruction signals to the aforementioned motor 6 through an interface 21, and receives the output signals of the position sensor 7 through the interface 21. A clock generator 22 releases scanning clock signals SC used as reference for the scanning with the laser beam 1. Said scanning clock signals SC are supplied to a scanning driver circuit 23 for driving the scanner 2 and also to the CPU 20 through the interface 21.

A detecting circuit 24 receives the photoelectric signals from the photoreceptor elements 11, 13, and, upon detection of foreign substances truly detrimental on the photomask 5, supplies detection signals SA, SB according to the status of the foreign substance to the CPU 20 through the interface 21.

In response to the output signal from the position sensor 7, the scanning clock signal SC and the detection signals SA, SB, the CPU 20 calculates the coordinate values of the area of the foreign substance on the photomask 5 and displays the result of said calculation on a display unit 25 through the interface 21. The display unit 25 is composed for example of a cathode ray tube which indicates a matrix map of the photomask 5, showing the area of the foreign substance with the indication of the size thereof for example in 3 ranks.

The detecting circuit 24 is provided with logic functions for exactly detecting the foreign substances alone according to the conditions explained already in relation to FIGS. 1 to 5. Said detecting circuit 24 will now be explained in more detail by a block diagram shown in FIG. 8.

Figure 8:
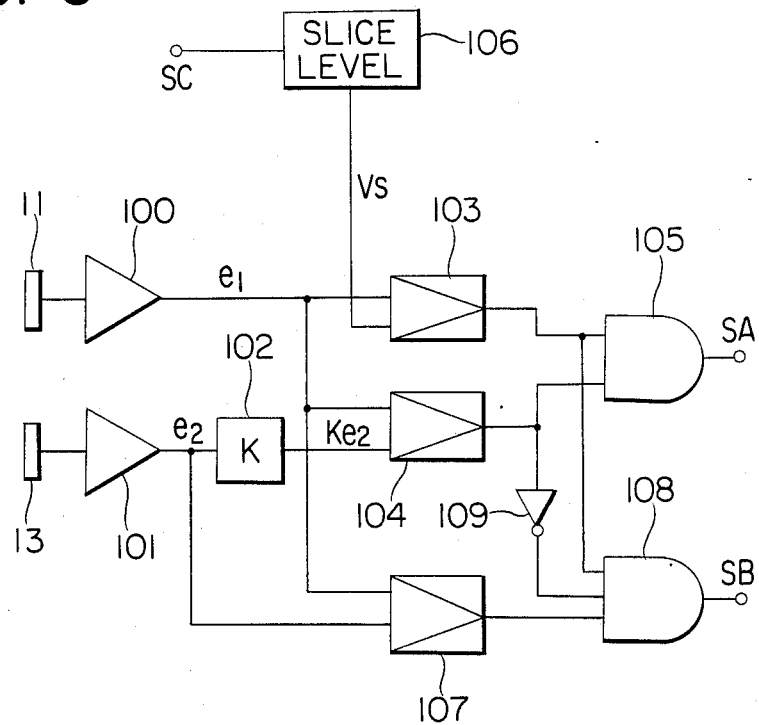
FIG. 8 is a block diagram of a detecting circuit adapted for use in the apparatus shown in FIG. 6.

In FIG. 8, the photoelectric signals from the photoreceptor elements 11, 13 are respectively supplied to amplifiers 100, 101, and an amplified photoelectric signal e1 is supplied to two comparators 103, 104 while the other amplified photoelectric signal e2 is supplied, through an amplifier 102 with an amplifying factor K, to the other input port of the comparator 104. The signals e1, e2 become mutually equal when the light intensities received by the elements 11, 13 are mutually equal. The other input port of the comparator 103 receives a slice voltage Vs from a slicing level generator 106. The output signals from the comparators 103, 104 are supplied to an AND gate 105. Said slicing level generator 106 varies the magnitude of the slicing voltage Vs in synchronization with the scanning clock signals SC for activating the scanner 2. The slicing voltage Vs is varied according to the irradiating position of the laser beam 1, since the distance from said position to the photoreceptor element 11 varies according to the scanning of the laser beam 1, thus varying the steric angle of the lens 10 for receiving the scattered light.

More specifically, as shown in FIG. 9, the projection of the optical axis of the lens 10 on the x-y plane forms an angle of 30° to 45° to the scanning area L. Thus, if the laser beam 1 maintains a constant power regardless of the scanning position, the scattered light received by the photoreceptor element 11 is strongest when the foreign substance is positioned at the left-hand end C3 of the scanning area L and becomes weaker as the position of the foreign substance moves to a central position C1 and to the right-hand end position C2.

Therefore the slicing voltage Vs is regulated, as shown in FIG. 10, highest when the laser beam 1 scans the position C3 and lowest when the laser beam 1 is at the position C2.

The amplifying factor K of the amplifier 102 is selected within a range from 1.5 to 2.5, for example 2. This is because, as already explained in relation to FIGS. 3 and 4, the ratio of the scattered light caused by a foreign substance adhered to the incident side of the laser beam and present in the space at the incident side to the scattered light passing through the photomask 5 is generally higher than 2.

The comparator 103 releases a logic signal "1" when the signal e1 is larger than the slicing voltage Vs. The comparator 104 compares the signal e1 with Ke2 obtained by multiplying the signal e2 with K, and releases a logic signal "1" when the former is larger. Consequently the AND gate 105 releases a detection signal SA of a logic value "1" when both of the comparators 103, 104 release the signals "1".

Another comparator 107 compares the signal e1 with the signal e2, and releases a logic signal "1" when the former is larger. A three-input AND gate 108 releases a detection signal SB of a logic value "1" when the output signal of the comparator 103, a signal obtained by inverting the output signal of the comparator 104 with an inverter 109 and the output signal of the comparator 107 are all at a logic value "1".

Now there will be explained the function of the above-described embodiment. In case a foreign substance is present on a face at the incident side of the laser beam 1, upon irradiation of said foreign substance by the laser beam 1, the signal e1 becomes larger than the slicing voltage Vs whereby the comparator 103 releases a signal "1". In this state the signal e1 becomes larger than Ke2 so that the comparator 104 also releases a signal "1". Thus the AND gate 105 generates the detection signal SA.

Then, in case a foreign substance is present on the rear face, the obliquely entering laser beam 1 is mostly reflected by the glass plate of the photomask 5 and only partially illuminates the foreign substance at the rear face. Thus the scattered light reaching the photoreceptor element 11 is smaller than that reaching the element 13 (e1<Ke2), so that the comparator 104 releases a signal "0". Consequently, even if e1 is larger than Vs in this state, the AND gate 105 remains closed. Also in case the scattered light is generated by an edge of the opaque area, the amounts of light received by the photoreceptor elements 11, 13 are sufficiently small because of the simple pattern, so that the comparator 103 releases a signal "0". Consequently the AND gate 105 remains closed. Thus the detection signal SA is not released in either case.

The magnitude of the slicing voltage Vs is related with the detecting power for the foreign substance, and the detection of a smaller foreign substance becomes possible as the slicing voltage Vs becomes smaller.

A detection signal SA from the AND gate 105 indicates the presence of a foreign substance adhered on a photomask face at the side of the photoreceptor 11 or the incident side of the laser beam. Such foreign substance is relative tall as illustrated as the foreign substance i in FIG. 5. On the other hand, in case of a low foreign substance which is not identified as a foreign substance by the AND gate 105, the comparator 104 may release a signal "0" through the photoelectric signal e1 is sufficiently large. In such case the AND gate 108 receives a signal "1" through the inverter 109 for inverting the output signal of the comparator 104. Also the comparator 103 releases a signal "1", since the signal e1 is sufficiently large, satisfying a relation e1>Vs. The comparator 107 releases a signal "1" since the photoelectric signal e1 is larger than the signal e2. Thus the AND gate 108 releases a detection signal SB of a logic level "1", indicating the detection of a relatively low foreign substance, or a scar on the glass plate, on a photomask face at the side of the photoreceptor element 11 or the incident side of the laser beam.

Naturally the absence of the detection signals SA, SB indicates the absence of foreign substances or scars on a face at the incident side of the laser beam.

In this manner the detection signal A and/or B assumes a logic value "1" only when a foreign substance is sticking to the front face (laser incident face) of the photomask 5. Moreover a detection signal SB "1" combined with a detection signal SA "0" indicates the presence of a low foreign substance m or a scar q as shown in FIG. 5, clearly distinguished from the usual foreign substance i.

In the comparator 107, the threshold ratio of the signals e1 and e2 for releasing a signal "1" is experimentally determined in relation to the shape of the foreign substance.

FIG. 11 shows a variation of the foregoing embodiment in which provided is a comparator 150 for comparing the signal e1 with a slicing voltage Vs' varying similarly with the slice voltage Vs and releasing, in case of e2>Vs', a logic signal "1" to AND gates 105, 108, whereby the detection is not made on a foreign substance present on the opaque area of the pattern but on a foreign substance present on a translucent area alone.

In the embodiment shown in FIG. 11, in case a foreign substance is present on a translucent area, the signals e1, e2 satisfy a relation e1>e2 and the signal e2 assumes a certain level. The slice voltage Vs' is so selected as to be smaller than said signal e2 in such state. Thus, in response to the presence of a foreign substance on a translucent area, the comparators 103, 104, 150 simultaneously release logic signals "1", whereby the AND gate 105 releases the detection signal SA.

On the other hand, a foreign substance present on an opaque area scarcely generates the scattered light on the rear face of the photomask 5 as already explained in relation to FIG. 1, so that the comparator 150 releases a logic signal "0" because of a state e2<Vs'. Therefore the AND gate 105 remain closed and the detection signal SA is not released.

In this manner the present embodiment allows to detect, among the foreign substances present on the translucent and opaque areas of the pattern, only the truly detrimental ones present on the translucent areas.

The foregoing embodiments has an advantage, in case of only detecting large foreign substances in a pattern with weak scattering, of identifying the foreign substances on the front face from those on the rear face and also identifying the shape of such foreign substances at a high speed, through the use of an extremely simple structure.

In the foregoing there have been explained the cases of entering the laser beam from a face bearing the circuit pattern for detecting the foreign substances present on said face. However, in a reticle or a mask utilized in a reduction exposure apparatus, not only the foreign substances on the pattern bearing face but also those on the rear face are detrimental to the exposure. If there is employed a reduction lens with a reduction ratio of 1/10, the minimum exposable size of the foreign substance present on the pattern-free rear face is about 1.5 times in length of about 2 times in area, of the minimum exposable size of that present on the patternbearing face. Consequently the foreign substances on the rear face should also be detected with an appropriate sensitivity. Such detection can be achieved by the apparatus of the foregoing first embodiment, wherein the photomask is reversed. In such case, however, the detection of foreign substances becomes difficult because of the enhanced effect of the light scattering from the edges of the opaque areas of the circuit patterns in case of a photomask with complicated circuit patterns.

Figure 12:
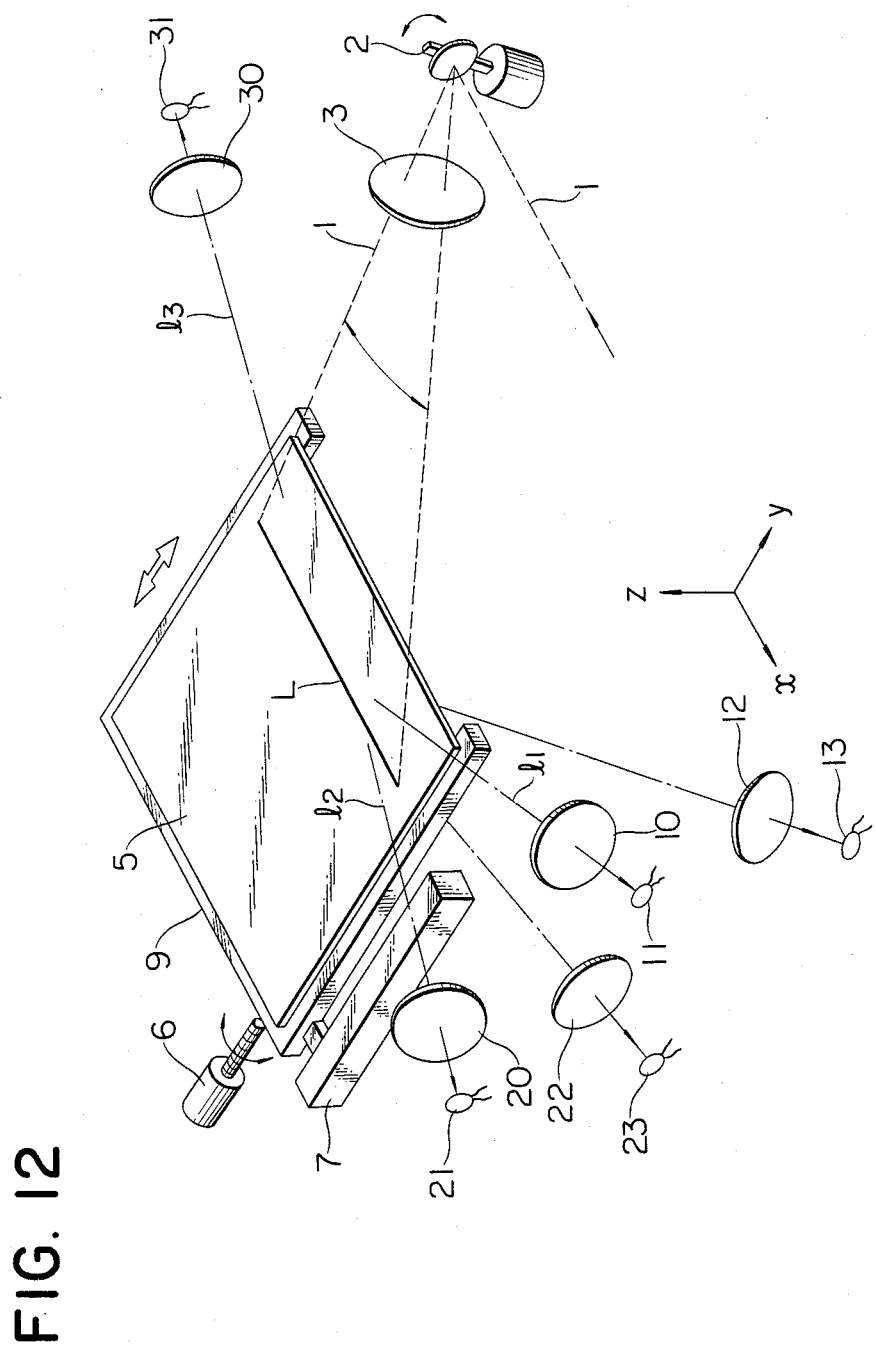
FIG. 12 is a perspective view of a third embodiment of the apparatus of the present invention.

An inspecting apparatus shown in FIG. 12 is different from that shown in FIG. 6, in that there are provided a pair of photoreceptor elements respectively looking at the front and rear faces of the photomask 5 and additional photoreceptor element in a redundant direction.

Said additional pair of the photoreceptors, respectively looking at the laser incident side and the rear side of the photomask 5 with substantially same light-receiving steric angles, is composed of a condenser lens 20 and a photoreceptor element 21 obliquely looking at the front side of the photomask 5 and a condenser lens 22 and a photoreceptor element 23 obliquely looking at the rear side of the photomask 5. The optical axes of the lenses 20, 22 are directed to the approximate center of the scanning area L, and lie on a plane containing the longitudinal x-direction of the scanning area L, parallel to the x-z plane.

Consequently the optical axes of the lenses 10 and 20 form an angle of 30° to 45°. A similar angle is formed between the optical axes of the lenses 22 and 12.

Additionally a condenser lens 30 and a photoreceptor element 31 are so positioned as to look at the pattern bearing face of the photomask 5 receiving the laser beam, from a direction opposite to the optical axes of said lenses 10, 20.

Figure 14:
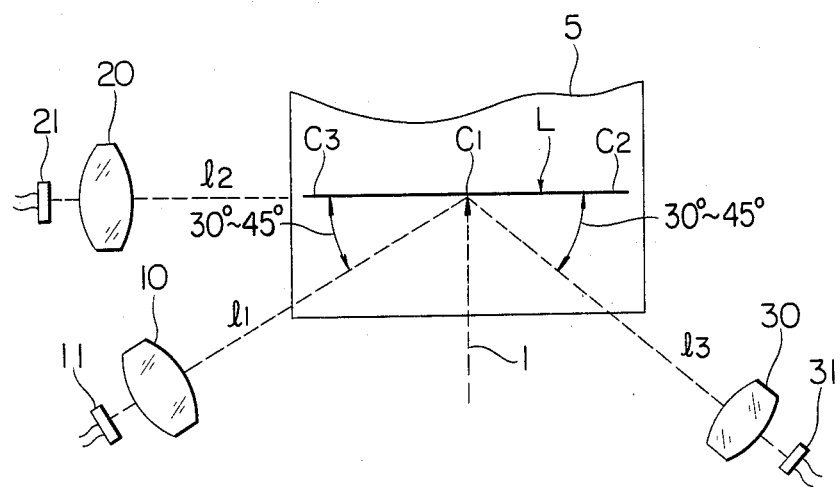
FIG. 14 is a plan view showing a part of the apparatus shown in FIG. 12.

There will now be given an explanation on the relationship between the optical axes of the lenses 10, 20, 30. It is assumed that said lenses 10, 20, 30 have same optical characteristics, and three photoreceptor elements 11, 21, 31 have same characteristics. The respective optical axes 11, 12, 13 all form a small angle, for example in a range from 10° to 30°, to the pattern bearing face of the photomask 5. Also the photoreceptor elements 11, 21, 31 are positioned at a same distance from the center of the scanning area L. When the photomask 5 is seen from above as shown in FIG. 14, the optical axis 12 lies on the longitudinal direction (scanning direction) of the scanning area L, while the optical axes 11, 13 form small angles, for example about 30°, to said scanning area L.

In such arrangement of the optical axes 11, 12, 13, the scattered light generated at the edge of the pattern is scarcely received in one of three photoreceptor elements 11, 21, 31. Also as a general rule, when the scattered light from the pattern edge is strongly received by the photoreceptor elements 11, 21, it is hardly received by the element 31. On the other hand, since the scattered light from a foreign substance is omnidirectional, the intensities of the lights received by the photoreceptor elements 11, 21, 31 are mutually almost same if the foreign substance is positioned at the center of the scanning range L.

The present embodiment therefore performs the inspection for foreign substances depending not only on a fact that the distributions of the scattered lights from the foreign substance and the circuit pattern are different in the space at the incident side of the laser beam, and also on a difference of the ratio of the scattered lights at the front and rear sides of the photomask 5 between the foreign substance and the circuit pattern.

Figure 13:
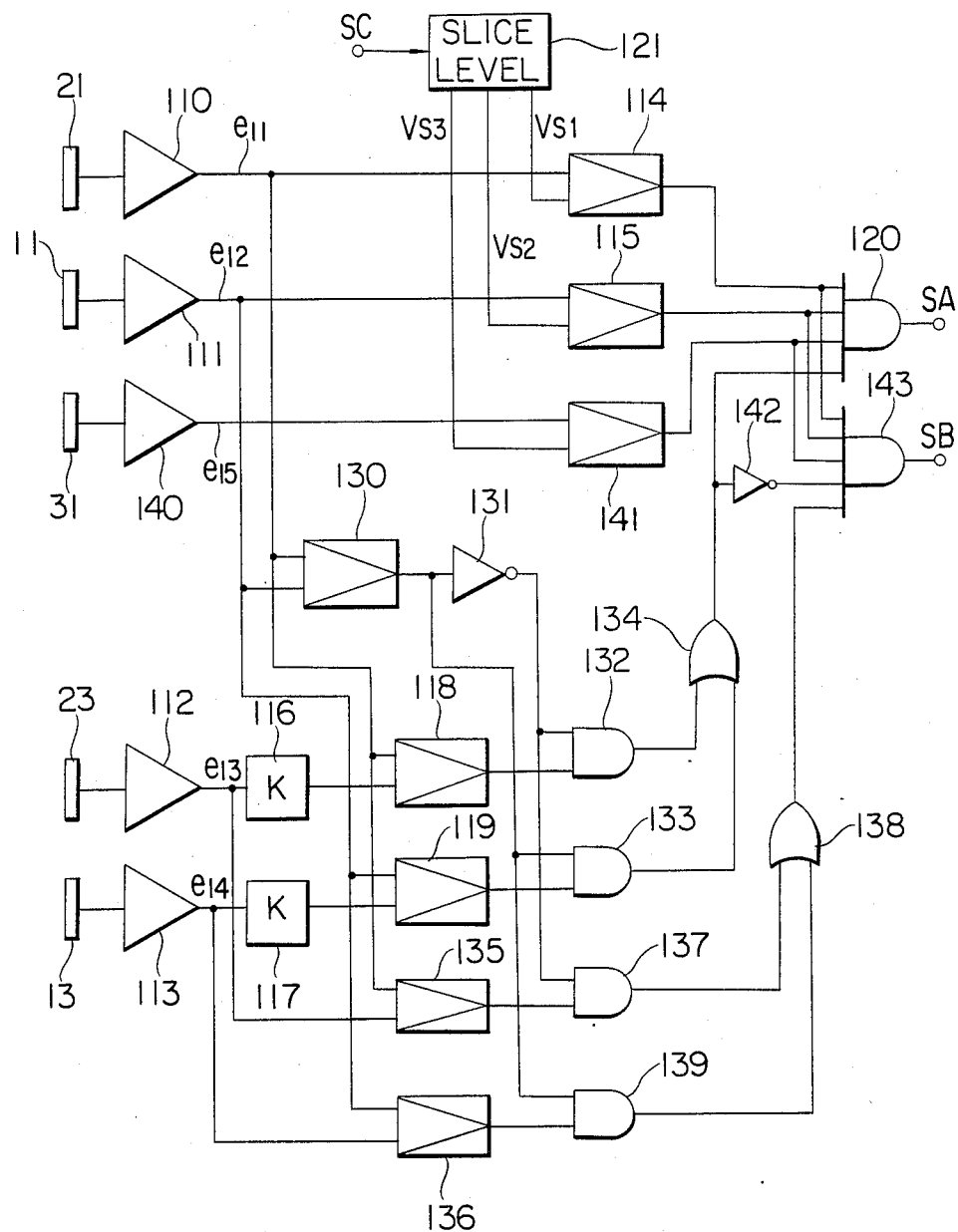
FIG. 13 is a block diagram of the detecting circuit adapted for use in the apparatus shown in FIG. 12.

In order to adapt to said embodiment, the testing circuit 24 shown in FIG. 7 is constructed as shown in FIG. 13. Photoelectric signals from photoreceptor elements 21, 11, 23, 13, 31 are respectively supplied to amplifiers 110, 111, 112, 113, 140, which are so constructed as to provide output signals e11, e12, e13, e14, e15 of a same level if said photoreceptor elements 21, 11, 23, 13, 31 receive the lights of a same intensity.

A comparator 114 compares the output signal e11 with a slice voltage Vs1 from a slice level generator 121, and releases a logic signal "1" in case of e11>Vs1. A comparator 115 compares the output signal e12 with a slice voltage Vs2 and releases a logic signal "1" in case of e12>Vs2. A comparator 141, receiving a slice voltage Vs3 supplied from the slice voltage generator 121 and varying in response to the scanning clock signals SC, namely according to the scanning position of the laser beam spot, releases a logic signal "1" in case the output signal e15 exceeds the slice voltage Vs3 and otherwise a logic signal "0".

Since the photoreceptor element 31 looks at the center of the scanning area L from a direction opposite to that of the photoreceptor elements 11, 21, the change of the slice voltage Vs3 is rendered opposite to that of the slice voltages Vs1, Vs2.

More specifically, if a foreign substance is present at the central position C1 of the scanning area L on the photomask 5 shown in FIG. 14, the afore-mentioned signals e11, e12, e13 have a substantially same magnitude since the photoreceptor elements 21, 11, 31 have a substantially same steric angle to the scattered light generated by said foreign substance. Thus the slice voltages Vs1, Vs2, Vs3 are selected as a same magnitude when the spot of the laser beam 1 is positioned at C1.

On the other hand, when the foreign substance is positioned at C2, the photoreceptor element 21 receives a stronger light than the photoreceptor element 11. The signal e12 becomes thus larger than the signal e11, so that the slice voltages have to so selected as to satisfy a relation Vs2>Vs1. However, since the position C2 is far from the photoreceptor elements 21, 11, the difference between the signals e11 and e12 is not large. Therefore the corresponding slice voltages selected smaller than those at the position C1 and so as to satisfy a relation Vs2>Vs1.

In case the foreign substance is positioned at C3 closest to the photoreceptor element 21, the signal e11 becomes very large, while the signal e12 becomes smaller than that for the position C1 or C2 because of a significant change in the steric angle of the photoreceptor element 11 when looking at the position C3 in comparison with the case of looking at the position C1 or C2. Thus the slice voltages are selected smaller than those for the position C1 and so as to satisfy a relation Vs1>Vs2 with a considerable difference. The slice voltage Vs3 is so selected as to have a opposite tendency to that of the voltage Vs2.

Figure 15:
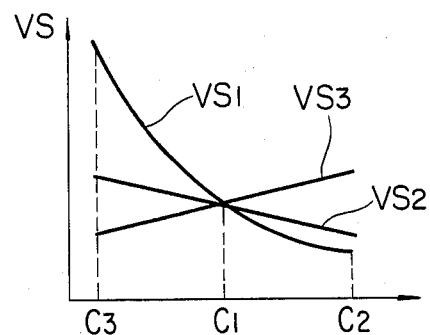
FIG. 15 is a chart showing the change in the slicing voltage.
Figure 16A:
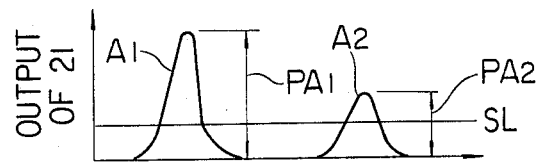
FIGS. 16A to 16D are wave form charts showing the output signals of the photoreceptors shown in FIG. 12.
Figure 16B:
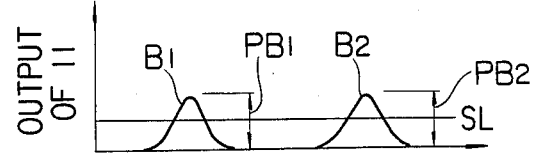
Figure 16C:
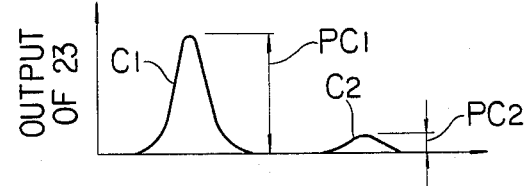
Figure 16D:
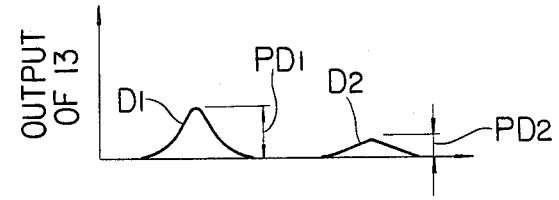

The above-described behaviors of the slice voltages for the positions C1–C3 are summarized in FIG. 15.

As explained above, the slice voltages Vs1, Vs2, Vs3 become mutually equal at the position C1, and continuously change so as to satisfy a relation Vs3>Vs2>Vs1 at the position C2 and a relation Vs1>Vs2>Vs3 at the position C3. The changes of said slice voltages Vs2, Vs3 are not necessarily linear but often assume curved forms in the same manner as in the case of the slice voltage Vs1. Such curved behavior may be obtained by incorporating a converting circuit of a logarithmic characteristic or a circuit for approximation with linear fractions into the slice level generator 121.

Again referring to FIG. 13, the output signals e13, e14 are respectively supplied to amplifiers 16, 117 of an amplification factor K, in order to distinguish the difference in the scattered lights at the front and rear sides of the photomask 5. Said amplification factor K is selected, as in the first embodiment, in a range from 1.5 to 2.5, for example 2.

A comparator 118 compares the output signal e11 with the output signal Ke13 of the amplifier 116, and releases a logic value "1" in case of e11>Ke13. A comparator 119 compares the output signal e12 with the output signal Ke14 of the amplifier 117, and releases a logic signal "1" in case of e12>Ke14.

In the present embodiment, among the photoreceptor elements 21 and 11 positioned at the incident side of the laser beam, either one with a smaller output is selected, and a discrimination is conducted whether the ratio of the outputs exceeds the constant K between thus selected photoreceptor element and a photoreceptor element positioned at the rear side and constituting the pair with the first-mentioned photoreceptor element.

The output signals e11, e12 of the amplifiers 110, 111 are supplied to a comparator 130, which releases a logic signal "1" or "0" respectively in case of e11>e12 or e11<e12. The output signal of said comparator 130 and an inverted output obtained through an inverter 131 are respectively supplied to input ports of AND gates 133, 132, of which the other input ports respectively receive the output signals from the comparator 118, 119. The output signals of said AND gates 132, 133 are supplied, through an OR gate 134, to an AND gate 120 for generatoring the detection signal SA. Said AND gate 120 also receives the output signals of the comparators 114, 115, 141.

A comparator 135 releases a logic signal "1" in case of e11>e13, while a comparator 136 releases a logic signal "1" in case of e12>e14. An AND gate 137 supplies the logic product of the output signal of the inverter 131 and the output signal of the comparator 135 to an OR gate 138, while an AND gate 139 supplies the logic product of the output signals of the comparator 130 and of the comparator 136 to the other input port of the OR gate 138. A 5-input AND gate 143 receives the output signal of the OR gate 138, a signal obtained by inverting the output signal of the OR gate 134 with an inverter 142, and the output signals of the aforementioned comparators 114, 115, 141 and generates the detection signal SB.

Now there will be given an explanation on the function of the circuit shown in FIG. 13 with reference to FIGS. 16A to 16D showing the change in the photoelectroc signals as a function of the scanning position of the laser beam spot in a similar manner as shown in FIGS. 4A and 4B.

In case the laser beam is scattered by an edge of the circuit pattern, the photoreceptor elements 21, 11, 23, 13 shown in FIG. 12 respectively provide output signals A1, B1, C1, D1 with respective peak values PA1, PB1, PC1, PD1 as shown in FIGS. 16A–16D. Since the scattered light is directional in this case, the peak value PA1 is larger than PB1, but the latter is not zero because the scattered light is not completely directional. The peak values PC1, PD1 from the photoreceptor elements 23, 13 at the rear side of the photomask 5 are respectively similar to the peak values PA1, PB1, as already explained in relation to FIG. 2. The photoreceptor element 31 does not receive the scattered light from the pattern edge. On the other hand, in case the laser beam is scattered by a foreign substance, said photoreceptor elements provide output signals A2, B2, C2, D2 with peak values PA2, PB2, PC2, PD2. Though the difference between the peak values PA2 and PB2 is small because the scattered light is less directional, but the peak values PA2, PB2 are considerably larger than the values PC2, PD2, with respective ratios of 2 to 8. In case of slicing the signals shown in FIGS. 16A and 16B with a slicing voltage SL smaller than the smaller one, for example PB1, of the scattered light from the circuit pattern to detect even the weak scattered light from a very small foreign substance, the circuit pattern will also be mistaken for a foreign substance. However, the foreign substance alone can be correctly identified even with such low slicing level SL by determining the ratio of the output signal of the photoreceptor element 21 to that of the element 23 and the ratio of that of the element 11 to that of the element 13, and identifying a foreign substance only when said ratios exceeds a certain value, for example 2, under a condition that the signals shown in FIGS. 16A and 16B exceed the slice level SL.

Now let us consider a case in which highly directional light scattering at the pattern edge is received more strongly by the photoreceptor element 11 than by the element 21. Naturally it is more weakly received by the element 31. Therefore the output signal e12 is larger than e11. Also as shown in FIG. 2, the amounts of light received by the photoreceptor elements 23, 13 are respectively equal substantially to the pairing photoreceptor elements 21, 11, so that the output signals e13 and e14 become respectively equal approximately to e11 and e12. Therefore e11<Ke13 and e12<Ke14, so that the comparators 118, 119 both release logic signals "0". Since e12>e11, the comparator 130 releases a logic signal "0" to close the AND gate 133. Thus the OR gate 134 releases a logic signal "0" so that the AND gate 120 releases a logic signal "0" in response to the scattered light from the pattern edge, even under conditions Vs1>e11, vs2>e12 and Vs3>e15.

On the other hand, in case scattered light is generated by a foreign substance attached to the pattern bearing face (incident side of the laser beam) of the photomask, the output signals e11, e12, e15 become respectively larger than the slice voltages Vs1, Vs2, Vs3, and the output signals e13, e14 respectively assume magnitudes of about ⅓-⅕ of those of the output signals e11, e12. Although said output signals e13, e14 are K-times amplified, there are obtained relations e11>Ke13 and e12>Ke14 since said amplifying factor K is determined within a range from 1.5 to 2.5.

Therefore the comparators 114, 115, 141, 118, 119 all release signals "1".

Also if e1>e2 in this state because of the state of scattering of the foreign substance, the comparator 130 releases a logic signal "1" to open the AND gate 133, thus releasing a signal "1". Thus the OR gate 134 releases a logic signal "1", whereby the AND gate 120 releases the detection signal SA "1".

In case the scattered light is generated by a foreign substance attached to the rear side of the photomask, the amounts of light received by the photoreceptor elements 23, 13 become respectively larger, as shown in FIG. 3, than those of the elements 21, 11. Consequently there always stand relations e11<Ke13 and e12<Ke14, so that the comparators 118, 119 release signals "0". Thus the AND gate 120 releases a logic signal "0" in response to a foreign substance attached to the rear side of the photomask.

In case of a foreign substance of a small height, even if attached to the front face, namely the incident side of the laser beam, the ratio of the amounts of light received by the photoreceptors elements 21 and 23 or those received by the elements 11 and 13 may not reach the constant K. In such case the scattered light from the foreign substance also appears strongly on the rear side of the photomask 5 to provide conditions e11<Ke13 and e12<Ke14, so that the comparators 118, 119 provide signals "0". Consequently the OR gate 134 provides a signal "0" regardless of the output signals of the comparator 130 and the inverter 131, whereby the AND gate 120 provides a signal "0" though the comparators 114, 115 and 141 release signals "1". In this manner the detection signal SA is not released in case of a foreign substance of a small height. The situation is same in case of a scar. On the other hand, the comparators 135, 136 respectively perform comparisons of the output signals e11 and e13, and of the output signals e12 and e14, and release signals "1" even for such foreign substance of small height because of conditions e11->e13 and e12>e14. Also depending on the relation of magnitude of the signals e11 and e12, either one of the AND gates 137, 139 is opened by the comparator 130 and the inverter 131, whereby the OR gate 138 releases a signal "1". Also the OR gate 134 releases a signal "0" for a foreign substance of a small height or for a scar to release a signal "1" from the inverter 142. Naturally the output signals e11, e12, e15 from the photoreceptor elements 21, 11, 31 positioned in the space of incident side of the photomask 5 become respectively larger than the slice voltage Vs1, Vs2, Vs3. Consequently the AND gate 143 receives signals "1" at all five input ports thereof, thus releasing the detection signal SB.

Such detection signal SB, in the absence of the detection signal SA, indicates the presence of either a foreign substance of a small height or a scar on the front face of the photomask 5. On the other hand, in case a highly directional light scattering is generated toward the photoreceptor element 21 from a pattern edge as shown in FIG. 16, the photoreceptor element 31 scarcely receives the scattered light. Thus the output signal e15 becomes smaller than the slice voltage Vs2, whereby the comparator 141 releases a logic signal "0".

Thus, even if the output signals from the comparators 135, 136 become unstable in response to the scattered light from the pattern edge to release a signal "1" from either of the AND gates 137, 139, the comparator 141 releases a signal "0" to provide a signal "0" from the AND gate 143.

As explained above, in the circuit of FIG. 13 equipped with the comparator 130, inverter 131 and AND gates 132, 133, the output signal of the OR gate 134 indicates the discrimination of either a foreign substance or a pattern edge through the ratio of the photoelectric signal from a photoreceptor element 21 or 11 receiving less light and the photoelectric signal from a photoreceptor element 23 or 13 paired with said less-light receiving element.

Thus, such selection of the smaller one of the output signals e11 and e12 signifies the selection of a light-receiving direction less affected by the light scattering from the circuit pattern, thus preventing disabled comparison of the photoreceptor systems of the front and rear sides of the inspected article due to the saturation of the signal processing system, particularly of the output signal of the amplifier, caused by a strongly directional scattered light received by the photoreceptor system of a particular direction from complicated circuit patterns, and providing an advantage of reducing erroneous detection of foreign substances in case the condenser lens systems looking at the front and rear sides of the inspected article contain certain geometrical errors in the arrangement thereof.

In the foregoing embodiments, the output logic signals from the comparators 118, 119 are determined by the sign of the subtractions (e11-Ke13) and (e12-Ke14). The functions of the foregoing embodiments can however be achieved also by a circuit in which the ratios of e11 to Ke13 and e12 to Ke14 are calculated for example with dividers and identified whether said ratios are larger than K.

It is furthermore possible to regulate the threshold height of the foreign substance if the amplification factor K of the amplifiers 116, 117 is rendered variable, and therefore possible to know the height of the foreign substance, or even the shape of the foreign substance or scar in relation to said amplification factor K. Also in order to inspect the rear face of the photomask 5, there may be provided, in the apparatus shown in FIG. 12, an optical path switching mirror or the like for obliquely introducing the laser beam 1 into the rear face of the photomask 5.

The status of presence of foreign substance inspected as explained in the foregoing is displayed on a display unit shown in FIG. 7, and the approximate dimension of the foreign substance can also be determined from the magnitude of the output signals e11, e12, e13, e14, e15 of the photoreceptor elements. It is therefore possible to indicate said dimension in approximate ranks, and to indicate the shape, whether tall or short, of the foreign substance, according to the status of the detection signals SA and SB.

Figure 17:
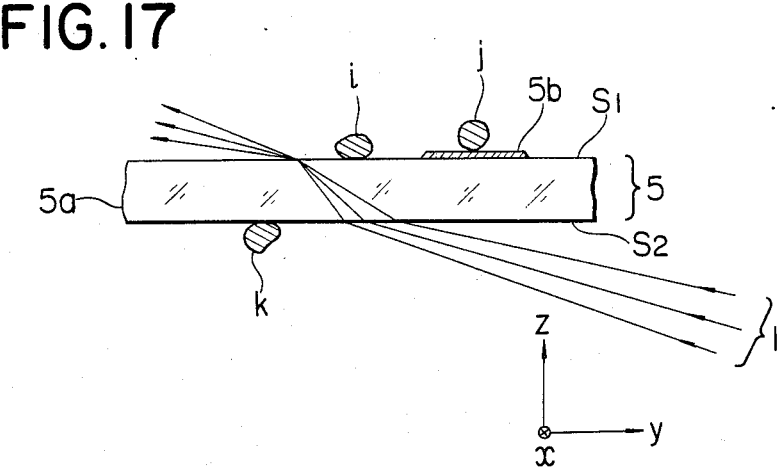
FIG. 17 is a view showing the relationship between the laser beam and the foreign substances present on the pattern bearing face and the opposite face of the glass substrate.
Figure 18:
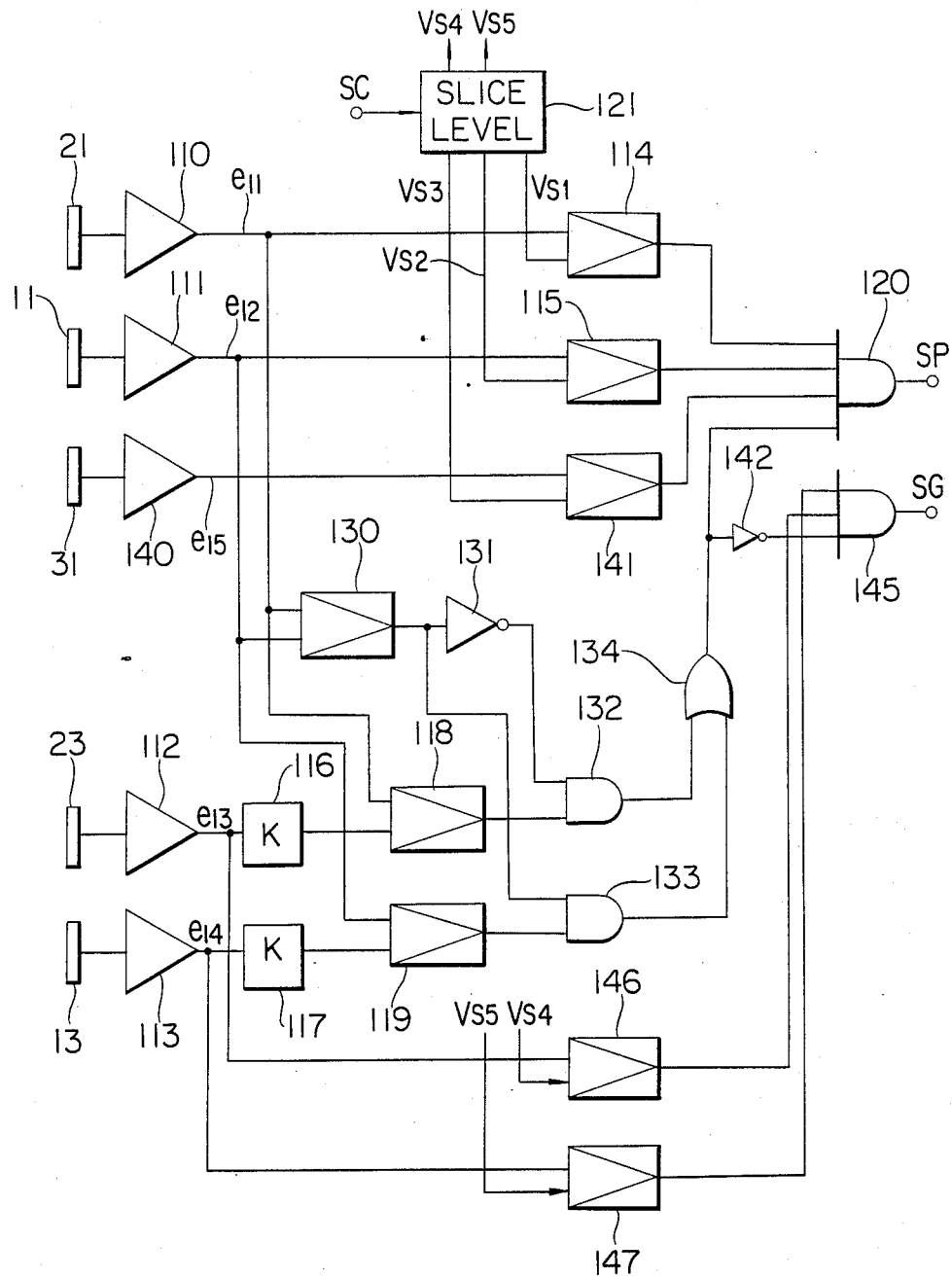
FIG. 18 is a block diagram showing a fourth embodiment of the detecting circuit.

FIGS. 17 and 18 show another embodiment capable of detecting foreign substances on both faces of the photomask by laser beam irradiation only from a side, without the use of an optical path switching mirror, thereby reducing the time required for inspection. FIG. 17 is a cross-sectional view of the photomask 5 seen from the x-direction, wherein the photoreceptor elements are positioned as shown in FIG. 12. In this case the laser beam 1, converging through the condenser lens 3, obliquely enters the lower face S2 of the photomask 5, then is focused on the pattern bearing face S1 through the glass plate 5a of the photomask 5, and proceeds again into the space.

The light scattering caused by foreign substances i, k present on the photomask 5 is already explained in relation to FIG. 3. More specifically, the scattered light generated in a space at a face where the foreign substance is present is stronger than that at the other face where the foreign substance is absent. On the other hand the foreign substance j present on the opaque area 5b of the pattern bearing face S1 does not cause light scattering since the laser beam is intercepted by the opaque area 5b.

FIG. 18 shows the detecting circuit for use in the present embodiment, where components of same functions as those in FIG. 13 are represented by same numbers. As explained in the foregoing embodiments, the photoreceptor elements 21, 11, 31 are positioned at the pattern bearing face S1 of the photomask 5, while the elements 13, 23 are positioned at the rear face S2. The amplification factor is selected within an approximate range from 0.5 to 2.0, for example K=1.0.

The slice level generator 121 generates, in addition to the slice voltage Vs1, Vs2 and Vs3, voltages Vs4 and Vs5 of which the levels are changed according to the scanning position of the laser beam, and which are respectively supplied to comparators 146, 147. The comparator 146 generates a signal "1" in case of e13>Vs4, while the comparator 147 generates a signal "1" in case of e14>Vs5. The outputs signals of said comparators 146, 147 are supplied to a 3-input AND gate 145 for generating a detection signal SG.

Now there will be explained the function of the above-described embodiment. In case a foreign substance is present on the pattern bearing face S1, corresponding to the foreign substance i on the glass plate 5a in FIG. 17, the scattered light from the foreign substance, caused by the laser beam irradiation through the glass plate 5a, is receieved by the five photoreceptor elements 11, 21, 31, 13, 23.

In this state, the signals e11, e12, e13 become respectively larger than the slice voltages Vs1, Vs2, Vs3 whereby the comparators 114, 115, 141 all release signals "1". On the other hand, the comparators 118, 119 respectively compare the photoelectric signals e11, e12 at the pattern bearing face S1 with the photoelectric signals Ke13, Ke14 at the rear face S2, and generate signals "1" because of conditions e11>e13 and e12>e14, since K=1.0. The comparator 130, inverter 131, AND gates 132, 133 and OR gate 134 preferentially the smaller one of the signals e11, e12 to the AND gate 120. More specifically the OR gate 134 releases a signal "1" in case of e12>Ke14 if e11>e12, or in case of e11>Ke13 if e12>e11. The AND gate 120, receiving signals "1" at all four input ports thereof, releases the detection signal SP indicating the presence of a foreign substance on the pattern bearing face S1. The detection signal SP is not generated by the light scattered from the edge of the opaque area 5b, since either one of the comparators 114, 115, 141 generates a signal "0" because of the directional nature of said light.

On the other hand, a foreign substance k attached to the rear face of the photomask 5, if alone irradiated by the laser beam, generates the signals e11, e12 larger than the signals e13, e14, whereby the comparators 118, 119 both release signals "0". Thus the AND gates 132, 133 release signals "0" to derive a signal "0" from the OR gate 134. Consequently the detection signal SP is not generated even if the signals e11, e12, e15 become larger than the slice voltages Vs1, Vs2, Vs3. On the other hand, the signals e13, e14 become larger than the slice voltages Vs4, Vs5 to generate signals "1" from the comparators 146, 147. The AND gate 145 therefore receives signals "1" at the three input ports thereof to release the detection signal SG. In this manner the detection signal SP, if not accompanied by the detection signal SG, indicates the presence of a foreign substance on the rear face S2 of the photomask 5.

In the following explained is a case in which scattered light is generated also from an edge of the opaque area 5b constituting the circuit pattern, when the foreign substance k attached to the rear face S2 is irradiated with the laser beam 1. It is assumed that the scattered light from the pattern edge is strongly directed toward the photoreceptors 21, 23 to realize a condition e11-

>e12. In this case the comparator 130 releases a signal "1" while the inverter 131 releases a signal "0", so that the AND gate 132 releases a signal "0". Consequently the output signal of the comparator 119 is preferentially employed. Since the foreign substance k is present on the rear face S2, there is obtained a condition e12<Ke14 (K=1), so that the comparator 119 releases a signal "0" while the AND gate 133 releases a signal "0", thus obtaining a signal "0" from the OR gate 134. In this manner the detection signal SG alone is generated to indicate the presence of a foreign substance on the rear face S2.

In order to determine the dimension of the foreign substance, it is necessary to know the magnitude of the photoelectric signals. In case the laser beam irradiation is made on both faces of the photomask by means of an optical path switching mirror as explained before, the photoelectric signals of the photoreceptor elements at the incident side may be used for this purpose. On the other hand, in the present embodiment, if the detection signal SP is generated indicating the presence of a foreign substance i on the pattern bearing face S1, the signals e11, e13 and e15 should be used for determining the dimension of the foreign substance. If the detection signal SG is generated indicating the presence of a foreign substance k on the rear face S2, the photoelectric signals e13, e14 should be used for this purpose. In order to achieve such objective, it is possible to introduce the output signals of first photoelectric means (photoreceptor elements 21, 11, 31) and those of second photoelectric means (photoreceptor elements 13, 23) respectively to A/D converters and to determine the signals to be used according to the status of the detection signals SP and SG.

In FIG. 17 the laser beam 1 is focused on the pattern bearing face S1 so that the intensity of light per unit area is naturally larger on said pattern bearing face S1 than on the rear face S2, with a larger detecting ability for the foreign substance on said pattern bearing face S1. Said focus point may be vertically displaced. Also there may be employed a parallel beam. It is therefore possible to regulate the detecting sensitivities on the pattern bearing face S1 and on the rear face S2 by the adjustment of said focus point.

A logic circuit for identifying the height of the foreign substance and for distinguishing a scar from a foreign substance as shown in FIG. 13 will further enable, if attached to the embodiment shown in FIG. 18, to divide the detection signal SP for the pattern bearing face into a detection signal SPA for a tall foreign substance and a detection signal SPB for a low foreign substance, and to divide the detection signal SG for the rear face into a detection signal SGA for a tall foreign substance and a detection signal SGB for a low foreign substance.

What is claimed is:

1. An apparatus for inspecting a planar translucent substrate for the presence of a foreign substance and/or a scar thereon, comprising:
   (a) irradiating means for obliquely introducing a light beam onto one surface of said substrate;
   (b) means for mutually displacing said irradiating means and said substrate in such a manner that the incident point of said light beam on said substrate scans said one surface;
   (c) first photoreceptor means positioned to face said one surface of said substrate and adapted to receive a part of the light randomly scattered at said substrate to generate a corresponding first electric output signal;
   (d) second photoreceptor means positioned to face the other surface of said substrate and adapted to receive another part of the light randomly scattered at said substrate to generate a corresponding second electric output signal;
   (e) comparator means for comparing said first and second electric output signals to discriminate which of predetermined plural relationships is satisfied by the mutual relationship of said first and second electric output signals and to generate a discrimination output signal; and
   (f) means for identifying the condition of said substrate according to the discrimination output signal of said comparator means.

2. An inspecting apparatus according to claim 1, wherein said identifying means comprises means for comparing the magnitude of at least either one of said first and second electric output signals with a reference value, and is adapted to respond to said discrimination output signal when said magnitude exceeds said reference value.

3. An inspecting apparatus according to claim 1, wherein said comparator means comprises first comparing means for producing an output when the ratio of said first and second electric output signals is positioned within a determined range, and a second comparing means for producing an output when said ration is positioned within another range.

4. An inspecting apparatus according to claim 1, wherein said comparator means comprises first amplifying means for amplifying said first and second electric output signals respectively with substantially same amplifying factors, second amplifying means for amplifying said first and second electric output signals with mutually different amplifying factors, a first comparator for comparing the first and second electric output signals amplified by said first amplifying means, and a second comparator for comparing the first and second electric output signals amplified by said second amplifying means.

5. An inspecting apparatus according to claim 4, wherein said second amplifying means is adapted to amplify said second electric output signal with a factor which is larger by a constant than the amplifying factor for said first electric output signal.

6. An inspecting apparatus according to claim 1, wherein said first photoreceptor means comprises a light-receiving face which is so positioned as to look obliquely with respect to said one surface of said substrate, and said second photoreceptor means comprises a light-receiving face which is so positioned as to be approximately symmetrical to the light-receiving face of said first photoreceptor means with respect to said substrate and to look obliquely with respect to the other surface of said substrate.

7. An inspecting apparatus according to claim 1, further comprising third photoreceptor means so positioned as to face said one surface of said substrate and adapted to generate a third electric output signal, and fourth photoreceptor means so positioned as to face the other surface of said substrate and adapted to generate a fourth electric output signal, wherein said third and fourth photoreceptor means are mutually positioned approximately symmetrical with respect to said substrate.

8. An inspecting apparatus according to claim 7, further comprising another means adapted to compare said third and fourth electric output signals to discriminate which of predetermined plural relationships is satisfied by the mutual relationship of said third and fourth electric output signals and to generate a discrimination output signal, wherein said identifying means is adapted to respond to said comparator means and to said another means.

9. An inspecting apparatus accoridng to claim 7, further comprising fifth photoreceptor means positioned to face a surface of said substrate and to be approximately opposite to said first photoreceptor means with respect to the incident point of said light beam.

* * * * *